(12) United States Patent
Phillips et al.

(10) Patent No.: US 7,998,076 B2
(45) Date of Patent: Aug. 16, 2011

(54) ADVANCED CHARACTERIZATION OF CONTRAST AGENTS WITH ULTRASOUND

(75) Inventors: Patrick J. Phillips, Sunnyvale, CA (US); James E. Chomas, San Francisco, CA (US); Ismayil M. Guracar, Redwood City, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1353 days.

(21) Appl. No.: 11/237,221

(22) Filed: Sep. 27, 2005

(65) Prior Publication Data

US 2007/0073146 A1    Mar. 29, 2007

(51) Int. Cl.
*A61B 8/14* (2006.01)
*A61B 8/00* (2006.01)
*G06K 9/00* (2006.01)

(52) U.S. Cl. ......... 600/458; 600/437; 600/443; 382/128
(58) Field of Classification Search .................. 600/458, 600/437, 420, 300, 443; 601/2; 382/128
See application file for complete search history.

(56) References Cited

U.S. PATENT DOCUMENTS

| | | | |
|---|---|---|---|
| 6,475,148 B1 | 11/2002 | Jackson et al. | |
| 6,494,841 B1 | 12/2002 | Thomas et al. | |
| 6,602,195 B1 | 8/2003 | Krishnan et al. | |
| 6,626,836 B2 | 9/2003 | Mao et al. | |
| 6,632,177 B1 | 10/2003 | Phillips et al. | |
| 6,638,228 B1 | 10/2003 | Brock-Fisher et al. | |
| 6,679,843 B2 | 1/2004 | Ma et al. | |
| 6,682,482 B1 | 1/2004 | Krishnan | |

FOREIGN PATENT DOCUMENTS

WO    WO 2006/015876    2/2006

OTHER PUBLICATIONS

Haider, Bruno and Chiao, Richard Y., "*Higher Order Nonlinear Ultrasonic Imaging*", 1999 IEEE Ultrasonics Symposium; pp. 1527-1531; dated Oct. 1999.
Tsutsui, M.D., Jeane M., et al., "*Detection of Retained Microbubbles in Carotid Arteries With Real-Time Low Mechanical Index Imaging in the Setting of Endothelial Dysfunction*", 2004 Journal of the American College of Cardiology; vol. 44, No. 5, 2004; pp. 1036-1046.
Zhao, Shukui et al., "*Radiation Force Assisted Targeting Facilitates Ultrasonic Molecular Imaging*", Jul. 2004 Molecular Imaging, vol. 3, No. 3; pp. 1-14.
Dayton, Paul A. et al. "*Optical and Acoustical Dynamics of Microbubble Contrast Agents Inside Neutrophils*", Mar. 2001, Biophysical Journal, vol. 80; pp. 1547-1556.
U.S. Appl. No. 10/899,803, filed Jul. 26, 2004.
EP Search Report from application No. 06121003.5-2305, dated Jan. 8, 2007, 7 pages.
Dayton, P A et al. Institute of Electrical and Electronics Engineers: *Ultrasonic enhancement of /spl Alph/v/spl beta/3 expressing-cells with targeted contrast agents*; 2003 IEEE Ultrasonics Symposium Proceedings, Honolulu, Hawaii, Oct. 5, vol. 1 of 2, Oct. 5, 2003, pp. 540-543.

*Primary Examiner* — Long V Le
*Assistant Examiner* — Katherine L Fernandez (57) ABSTRACT

Contrast agents are characterized with ultrasound. Flowing or unbound contrast agents are distinguished automatically from bound or relatively stationary contrast agents. The bound or relatively stationary contrast agents are highlighted on a display. A processor distinguishes different types of contrast agents or contrast agents in different binding states with relative signal strength or velocity. Attached contrast agents are differentiated from phagocytosed contrast agents. Monitoring absolute signal strength as a function of time may indicate binding. Any one or more of these features may be used.

17 Claims, 3 Drawing Sheets

FIG. 5

ADVANCED CHARACTERIZATION OF CONTRAST AGENTS WITH ULTRASOUND

BACKGROUND

The present embodiments relate to characterizing contrast agents. In particular, ultrasound distinguishes between different contrast agents, such as different types or different binding states.

Information at nonlinear frequencies, such as a cubic or nonlinear fundamental frequency, is detected by varying the transmit amplitude and phase associated with combined echo signals. Some techniques for detecting nonlinear fundamental information are disclosed in U.S. Pat. Nos. 6,494,841, 6,602,195, 6,632,177 and 6,682,482, the disclosures of which are incorporated herein by reference. The same or other nonlinear detection technique, such as phase or pulse inversion or pulse inversion Doppler, detects second harmonic nonlinear information. The nonlinear information, such as the nonlinear fundamental and second harmonic information, is generally specific to ultrasound contrast agents since contrast agents produce stronger nonlinear response and the transducer and tissue produce less nonlinear response. Some nonlinear detection techniques are more specific to contrast agents like those that detect nonlinear fundamental signals. The information provides improved tissue clutter rejection, allowing for imaging more specific to contrast agents. For example, small vessels within tissue may be more easily imaged or identified using nonlinear fundamental information.

U.S. Pat. No. 6,638,228, the disclosure of which is incorporated herein by reference, provides for contrast agent enhanced color-flow imaging. Power modulation or amplitude variation of the transmit pulses is used to obtain velocity information about moving contrast agents. A color Doppler estimator is used to detect the nonlinear signals from contrast agents with the purpose of suppressing signals from stationary or slowly moving objects.

Academic researchers and clinicians are working with contrast agents to detect, monitor response to therapy, and deliver drugs to diseased tissue such as atherosclerotic plaques in arteries. These studies utilize standard contrast agents as well as specially designed targeted contrast agents that bind to corresponding proteins on the endothelium or plaque. As one of many examples where contrast agents can be indicative of more than just where blood is flowing, contrast agents can attach to damaged endothelial cells within a vessel. Scanning electron microscopy and ultrasound contrast agent nonlinear fundamental information show contrast agents attached to a pig's carotid when the endothelium was damaged. Increased enhancement in contrast agent ultrasound detection is observed on the wall of the vessel. No contrast agents were observed attached to the control (non-injured) endothelium.

BRIEF SUMMARY

By way of introduction, the preferred embodiments described below include methods, systems, computer readable media and instructions for characterizing contrast agents with ultrasound. Flowing or unbound contrast agents are distinguished automatically from bound or relatively stationary contrast agents. The bound, phagocytosed, or relatively stationary contrast agents are highlighted on a display. Phagocytosed agents may be distinguished from attached agents. A processor distinguishes different types of contrast agents or contrast agents in different binding states with relative signal strength or velocity. Monitoring absolute signal strength as a function of time may indicate binding. Any one or more of these features may be used.

In a first aspect, a method characterizes contrast agents with ultrasound. Relatively rapidly moving contrast agents are distinguished from stationary or relatively slowly moving contrast agents with a processor responsive to ultrasound signals. Information from the stationary or slowly moving contrast agents is highlighted relative to the rapidly moving contrast agents.

In a second aspect, a computer readable storage medium has stored therein data representing instructions executable by a programmed processor for characterizing contrast agents with ultrasound. The instructions are for rejecting information associated with flowing contrast agents, identifying information associated with bound, attached, or phagocytosed contrast agents, and generating an image as a function of the information associated with bound contrast agents.

In a third aspect, a method characterizes contrast agents with ultrasound. A relative strength of two or more nonlinear frequency components of ultrasound signals responsive to contrast agents is determined automatically. An image is generated as a function of the relative strength.

In a fourth aspect, a method characterizes contrast agents with ultrasound. Signal strength of contrast agents in a region is monitored as a function of time with ultrasound. An image is generated as a function of signal strength at different times.

The present invention is defined by the following claims, and nothing in this section should be taken as a limitation on those claims. Further aspects and advantages of the invention are discussed below in conjunction with the preferred embodiments and may be later claimed alone or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

For targeted drug delivery, it is desirable to detect a region where the bubbles have been captured, such as detecting contrast agents captured on atherosclerotic plaque. A drug-delivery pulse of ultrasound is delivered to the region. Contrast agents bound to the targeted area are broken to release drugs or increase uptake while minimizing the breakage of contrast agents in other regions, such as free-flowing contrast agents. This approach reduces systemic delivery and increases relative delivery to the targeted area compared to the rest of the body.

Academic research and/or clinical markets may use targeted contrast agents. Imaging contrast agent attachment and drug delivery efficiency may be desired. By characterizing contrast agents by type or state, direct 'delivery' ultrasound pulses are guided in space and time. Other uses may be provided.

Non-moving contrast agents are detected, and regions where non-moving contrast agents are detected are color coded or highlighted to the user. One differentiator between contrast agents that have attached to the endothelium or phagocytosed compared to those that are free is the velocity of the contrast agent. Free flowing contrast agents tend toward the center of a vessel because the lowest shear rate is in the middle of the vessel. Velocity identifies bound contrast agents since free contrast agents likely do not remain on the edge of a vessel in a slowly moving or stationary condition. The combination of velocity information and detected signal information can better discriminate between bubble types or bubbles that are attached or captured.

Alternatively or additionally, the ratio of two or more nonlinear frequency components identifies contrast agents more specifically. Colors are assigned to unique values of the ratios and superimposed on an image.

Alternatively or additionally, changes in the received echoes due to attachment are detected. Contrast agents bound to the endothelium, phagocytosed by white blood cells, or tethered to any physiologic boundary exhibit different behavior than free contrast agents due to the change in the boundary condition around the contrast agent. This change in boundary condition may increase the resonant frequency and reduce the received echo intensity compared to free contrast agents. The change in boundary condition in a contrast agent bound to the endothelial wall generates a narrowband component near the transmitted center frequency in addition to higher frequency components. In comparison, a free contrast agent generates a wider band response. The signal from contrast agents taken into cardiac myocytes decreases in signal amplitude compared to free bubbles.

Figure 1:
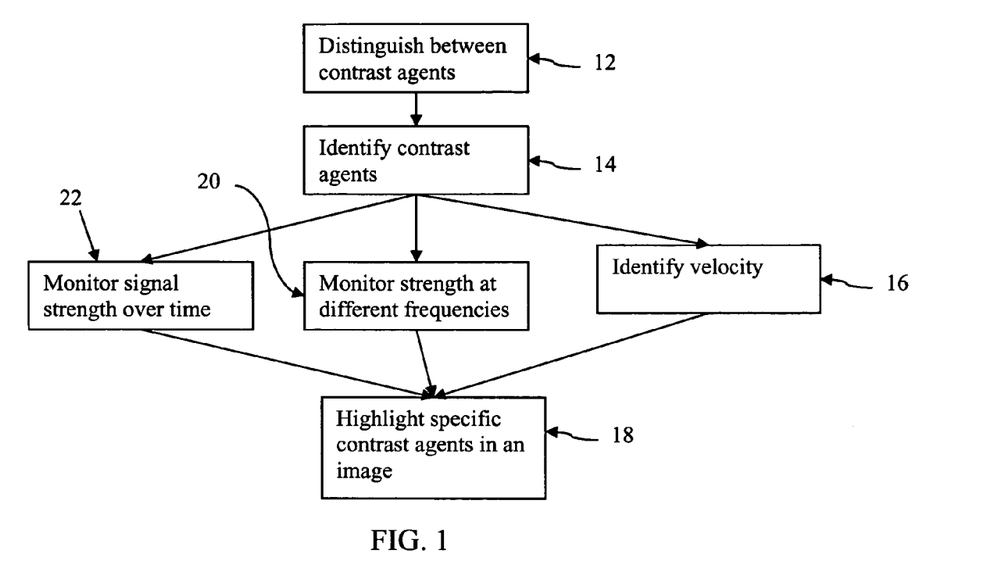
FIG. 1 is a flow chart diagram of one embodiment of one or more methods for characterizing contrast agents.

FIG. 1 shows a method for characterizing contrast agents with ultrasound. The method includes three different approaches to characterizing the same or different types, states or other characteristics of contrast agents. One approach monitors changes in signal strength (act 22), another monitors signal strength at different frequency bands (act 20) and the other identifies velocities associated with contrast agents (act 16). The three different approaches are used separately or in any combination of two or more. Other approaches may be provided, such as determining an absolute value. Additional, different or fewer acts may be provided, such as using any of the approaches with or without highlighting or imaging.

In act 12, a processor collects information about and distinguishes between contrast agent characteristics. Any distinction may be of any property. For example, ultrasound response distinguishes between different types of contrast agents, different sizes of contrast agent, different states of contrast agent (e.g., free flowing, bound, attached, or phagocytosed), or different contents of contrast agents. The distinction is performed automatically, such as by a processor in response to user activation of a drug delivery or other contrast agent related application. User input may assist the processor, such as the user inputting the types of contrast agents for assisting automatic identification of different contrast agents.

The processor is responsive to ultrasound signals. Acoustic energy is transmitted. Some of the acoustic energy reflects from the contrast agents within a patient. To avoid destruction of the contrast agents, the transmitted energy has a low mechanical index, has a frequency or has another power characteristic (e.g., pulse length) less likely to destroy the contrast agents. Alternatively, the acoustic energy has a higher mechanical index purposefully destroying or bursting contrast agents or resulting in acceptable destruction.

The contrast agents are applied intravenously or through other techniques. Any now known or later developed contrast agent may be used. The contrast agents are microspheres, microbubbles or other small structures which respond to acoustic energy by bursting, vibrating or reflecting the energy. The contrast agents may include or be formed from materials or substances with medicinal qualities, such as a medication for breaking up plaque or interacting with specific tumors or other cell types. Alternatively, the contrast agents have no medicinal substances. More than one type of contrast agent may be in the patient. The contrast agents are applied during an imaging session, such as a 15 minute to one-hour procedure for examining a patient during a visit or medical procedure.

In one approach represented by acts 14 and 16, the contrast agents are distinguished between flowing contrast agents and bound contrast agents. Bound agents may be attached to cells or phagocytosed by cells. Information from the flowing contrast agents is rejected, not used or relatively reduced in influence, and information from the bound contrast agents is identified, or vice versa. Bound contrast agents are stationary or relatively slowly moving as compared to free flowing contrast agents. Fluids, such as blood, continuously or periodically move faster than the tissue or other structures adjacent to the blood. Contrast agents bound to the tissue or other structure move slower than contrast agents flowing with the blood or do not move. Signal from stationary or slowly moving contrast agents may then be highlighted in act 18. Differentiation may also be made between agents that are attached versus phagocytosed by using different highlighting.

In act 14, ultrasound energy from contrast agents is separated or distinguished from ultrasound energy from tissue or fluid. The distinction or separation identifies the contrast agents relative to fluid and/or tissue. Second harmonic imaging, such as with filtering or pulse inversion, may be used. Contrast pulse sequencing (CPS) that detects nonlinear fundamental energy may be used. Other now known or later developed techniques providing contrast between tissue and/or fluid from contrast agents may be used.

In one embodiment, the contrast agent detection techniques disclosed in one or more of U.S. Pat. Nos. 6,494,841, 6,602,195, 6,632,177, 6,682,482, 6,638,228, or 7,004,906 (application Ser. No. 10/899,803 (Publication No. 2006/0036174)), the disclosures of which are incorporated herein by reference, are used. Flowing and bound contrast agents are located as a function of nonlinear (e.g., cubic) fundamental or other nonlinear response. Nonlinear fundamental signals responsive to contrast agents are detected by combining the ultrasound signals received in response to transmissions with different amplitude levels, such as in response to transmission of three or more pulses (i.e., triplet). For example, energy at the nonlinear or cubic fundamental is primarily, substantially or almost entirely responsive to contrast agents. The energy at the nonlinear or cubic fundamental includes less, little or no response to tissues or fluid. The transmit, receive and combination of different pulses identifies contrast agents from tissue and fluids. By using different amplitudes and/or phases on transmit and/or receive, the desired response characteristics may be provided.

In act 16, the velocity of the contrast agents is identified. A sequence of or multiple triplets (or other subset) are transmitted to identifying contrast agents. A sequence of received signals representing nonlinear fundamental or harmonic response of contrast agents with less information from tissue or fluid results. For example, a color Doppler like sequence disclosed in U.S. Pat. Nos. 7,004,906 or 6,638,228 is used. Detection of the nonlinear fundamental or other harmonic is repeated, providing a sequence of data for motion estimation. The sequence of information allows detection of motion in nonlinear fundamental signals uniquely generated by contrast agents. Since tissue is rejected in act 14, velocity estimation of contrast agent is performed with non-linear fundamental signals (i.e., contrast agents only). Other sequences of information from act 14, such as second harmonic or linear fundamental corresponding to identified contrast agents, may be used to estimate velocities.

Using Doppler processing, correlation or other estimation, the velocities of the flowing and bound contrast agents are estimated. To distinguish bound contrast agents from flowing contrast agents, information from contrast agents above a threshold velocity is removed or reduced. A clutter filter set to reduce high velocities, such as associated with Doppler tissue imaging, may alternatively isolate or relatively enhance information from bound contrast agents. Velocity parameter estimates are used to reject the signal from moving contrast agents and highlight stationary or relatively slowing moving contrast agents.

In one embodiment of acts 14 and 16, a sequence of pulses is transmitted (TX). The sequence of pulses is transmitted along or adjacent to a scan line, L1. The sequence of pulses is used to form a plurality of samples for estimating velocity of contrast agent as a function of the cubic fundamental of the echo signals. The velocity is responsive to echoes from each of the pulses of the sequence.

Cubic fundamental signals can be obtained by transmitting an exemplary three pulses with varying amplitude and phase. A plurality of pulses having at least two different amplitude levels and at least two of the plurality of pulses having opposite phases are transmitted. For example, the sequence of pulses to obtain cubic fundamental information for a single sample for each depth location along a line is represented as [½ -1 ½]. The magnitude (i.e., ½ versus 1) represents amplitude and the polarity (i.e., negative versus positive) represents the relative phasing, here a 180 degree difference. [½ 1 ½] as well as other sequences with or without polarity changes or with different amplitude differences may also be used. It is preferred that the ½ amplitude pulses are achieved by using a subset of the full aperture, such as even or odd elements of the aperture, so may be represented as ½e for the even elements and ½o for the odd elements. Other aperture groupings to obtain the desired amplitude may be used.

A sample is formed by combining signals responsive to the transmitted pulses. In one embodiment, the signals for each pulse are equally weighted and summed, but unequal weighting with or without phase shifts may be performed for the combination of received signals. A sample is represented as $Y_N$. Each sample is formed from a unique combination. In one embodiment, the transmit pulses used for a given sample are used only for that sample. Alternatively, one or more pulses are used for different samples. Table 1 shows a contrast pulse transmit sequence along one scan line with receive filtering using shared pulses.

TABLE 1

| | Transmit sequence | | | | |
|---|---|---|---|---|---|
| Received point | ½e $X_0$ | −1 $X_1$ | ½o $X_2$ | −1 $X_3$ | ½e $X_4$ |
| Receive weight $Y_0$ | 1 | 1 | 1 | | |
| Receive weight $Y_1$ | | 1 | 1 | 1 | |
| Receive weight $Y_2$ | | | 1 | 1 | 1 |

The $X_n$ corresponds to the order of transmission of the five pulses along the scan line. The "1" values are the weights applied to receive signals. The location of the "1" corresponds to the transmit pulses and associated received signals to be weighted. In table 1, three sets of samples $Y_0$, $Y_1$ and $Y_2$ for a same scan line are output.

The three samples are output from the filter block into the detector, such as a color Doppler autocorrelation detection processor. The velocity is estimated in act 16 as a function of the three samples or combined signals.

The $Y_1$ samples of Table 1 may have poor linear fundamental rejection, and may contaminate the detected agent energy and velocity estimates. The input receive signals may be reordered for input to a fixed clutter filter, and color Doppler detection performed with two desired points. Table 2 represents using the same transmit sequence, but reordering the resulting received signals for combination into two sets of samples.

TABLE 2

| | Transmit sequence | | | | |
|---|---|---|---|---|---|
| Received point | ½e $X_0$ | ½o $X_2$ | −1 $X_3$ | −1 $X_1$ | ½e $X_4$ |
| Receive weight $Y_0$ | 1 | 1 | 0 | 1 | |
| Receive weight $Y_1$ | | 1 | 1 | 0 | 1 |

Alternative methods to discard or avoid the undesired output samples include decimation filtering and generalized matrix filtering. Other desired combinations responsive to cubic fundamental information input to the autocorrelation operation may be used.

Many sequences can be used to compute cubic fundamental sensitive contrast agent velocity. Additional points can be added to the sequences to improve the quality of the velocity estimates, such as shown in table 3.

TABLE 3

| Transmit sequence | Clutter filter | Est. samples | reorder pattern |
|---|---|---|---|
| ½e −1 ½o −1 ½e | [1 0 1 1] | 2 | 0, 2, 3, 1, 4 |
| ½e −1 ½o ½e −1 ½o | [1 0 1 0 1] | 2 | 0, 2, 4, 1, 3, 5 |
| ½e −1 ½o ½e −1 ½o ½e −1 ½o | [1 0 0 1 0 0 1] | 3 | 0, 3, 6, 1, 4, 7, 2, 5, 8 |
| ½e 1 ½o 1 ½e | [−1 0 1 1] | 2 | 0, 2, 4, 1, 3 |

In table 3, the estimate samples represent the number of sets of combined signals or samples output for velocity estimation. The clutter filter represents the weighting for a moving window applied to the received signals of the transmit pulses to obtain the samples. The reorder pattern is provided to present the desired data to the clutter filter for forming the samples. Other orders may be used.

Sequences may be adapted to provide improved sensitivity for low velocities in act 14. The pulses are spaced unequal distances apart in time within the sequence. For example, pulses for detection of cubic fundamental information are transmitted closer together in time than pulse sets for estimation of the velocity. Since different transmitted pulses are used for different samples, the sequence of pulses along a line or adjacent lines may provide pulses used for each sample at a high rate (i.e., relatively close spacing in time), but with the pulses for different samples used for velocity estimation spaced farther apart in time.

In one embodiment, the spatial distribution of pulses of a sequence is obtained by interleaving pulses for other sequences. For example, pulses of a sequence used for forming samples on different, such as adjacent, scan lines are transmitted interleaved with pulses for a given scan line. The interleaving provides for a different number of pulses from other sequences being between two different sequential pairs of the pulses of a given sequence, resulting in variation of the time between pulses of the given sequence where a sequence is associated with pulses for two or more samples to be used for estimating a velocity.

In one embodiment for interleaving, equal spacing in time between the pulses is used. This interleaving is similar to interleaving for low velocity scale settings for conventional color Doppler. For example, if the flow sample interleave ratio (FSIR) is 3 (i.e., data for three spatially distinct scan lines are acquired in an interleaved fashion) and the sample count (i.e., number of pulses per scan line) is 6, then the total of 18 firings are acquired with the following ordering:

```
spatial line: 1 2 3 1 2 3 1 2 3 1 2 3 1 2 3 1 2 3
              |-PRI-|
```

By convention, the PRI is defined as the time interval between pulses for the same spatial location. It corresponds to the velocity scale set by the user. A 6-pulse contrast pulse sequence with the same interleaving sequence showing the aperture-weighting pattern is provided as:

$$1^{(1/2e)} 2^{(1/2e)} 3^{(1/2e)} 1^{(-1)} 2^{(-1)} 3^{(-1)} 1^{(1/2o)} 2^{(1/2o)} 3^{(1/2o)}$$
$$1^{(1/2e)} 2^{(1/2e)} 3^{(1/2e)} 1^{(-1)} 2^{(-1)} 3^{(-1)} 1^{(1/2o)} 2^{(1/2o)} 3^{(1/2o)}$$

The time between individual firings is PRI/3, or more generally PRI/FSIR.

By acquiring contrast pulse sequences with a long PRI, the velocity resolution for low velocities is increased. For example, the sample correlation is between complex clutter filter output samples that are 3*PRI apart in time. Sensitivity to linear fundamental clutter may be increased in the interleaving cases as well as the possibility of incoherence due to motion within the three pulses of the coherently combined triplet (i.e., three pulses used to form one set of samples along a scan line) because of the longer PRI. To avoid this unwanted sensitivity, the pulses used for a given sample are maintained closer in time, providing unequal temporal spacing of pulses of the sequence. For example, at least six first pulses are transmitted. The six pulses correspond to two triplets or two sets of pulses where each set has at least two pulses with different amplitude levels and at least two pulses with different phases. Three pulses (i.e., a first triplet) in the sequence corresponding to a first set of samples are transmitted free of interleaving. Pulses for one or more other sequences are than transmitted. Then, three more pulses (i.e., a second triplet) in the original sequence corresponding to a second set of samples are transmitted free of interleaving. This example sequence is represented by:

$$1^{(1/2e)} 1^{(-1)} 1^{(1/2o)} 2^{(1/2e)} 2^{(-1)} 2^{(1/2o)} 3^{(1/2e)} 3^{(-1)}$$
$$3^{(1/2o)} 1^{(1/2e)} 1^{(-1)} 1^{(1/2o)} 2^{(1/2e)} 2^{(-1)} 2^{(1/2o)} 3^{(1/2e)}$$
$$3^{(-1)} 3^{(1/2o)}$$

```
|-----3*PRI used for velocity estimate------|
```

This example sequence preserves high sampling rates for the triplets while retaining the long correlation intervals for velocity sensitivity. Good linear fundamental clutter rejection is maintained because the second difference clutter filtering in this example is performed at a high sample rate (PRI/3). Increased velocity resolution is provided by the sample interleaving because the autocorrelation is performed across samples that are 3*PRI apart in time. Stationary and moving contrast agent may be better differentiated because of the greater velocity resolution.

In alternative embodiments, sets of four or more pulses are used instead of triplets (i.e., sets of three pulses) to acquire a given sample. In yet other embodiments, some interleaving is provided within the triplet or set of pulses for combination to obtain the cubic fundamental information. More or less relative interleaving is provided between the sets of pulses than shown in the example above or than used within the sets or triplets. In one embodiment, the pulses of a set used for obtaining cubic fundamental information are interleaved with another set in the same sequence. In yet another alternative embodiment, one or more pulses of a sequence are used for generating two or more samples.

Received signals responsive to each set of transmitted pulses are combined. The combination is performed as discussed above to obtain a sample or samples along a scan line responsive to cubic fundamental information. Received signals responsive to the different amplitude and phased pulses are combined to obtain cubic fundamental information. In the example above, received signals responsive to the first triplet (i.e., the first three pulses labeled "1") are combined, and the received signals responsive to the second triplet (i.e., the last three pulses labeled "1") are combined. By combining the received signals for each of the two or more sets of pulses in a sequence, two or more samples are generated for each given spatial location.

Velocities are estimated as a function of cubic fundamental signals responsive to the pulses of the sequence. The velocity at a given spatial location is estimated from the two or more samples formed from the sequence of transmit pulses. For example, a velocity is estimated from the two samples obtained using the "1" sequence transmit pulses in the example above. The velocities distinguish between bound and flowing contrast agents.

In another embodiment of acts 14 and 16, linear fundamental information is used to distinguish bound from flowing contrast agents. Locations of the scanned region corresponding to contrast agents are located. Contrast agents are distinguished from fluid or tissue as discussed above for act 14. Velocities are estimated from linear fundamental information. Pulses for velocity estimation are interleaved with pulses for identifying stationary or slowly moving contrast agents. One or more pulses may be used for both velocity estimation and stationary or slowly moving contrast agent identification. Locations corresponding to stationary or slowly moving contrast agents with low or no velocity are identified as bound contrast agents. Moving fluid related velocity information may be removed by a velocity of flow threshold. Higher velocities are more likely associated with non-bound contrast agents.

In act 18, an image is generated as a function of the distinguished characteristic. For example with acts 14 and 16, the image is generated as a function of the information associated with bound contrast agents. Information from the stationary or slowly moving contrast agents are highlighted relative to the rapidly moving contrast agents. In one embodiment, the information from rapidly moving contrast agents is not used or provided in the image. The information from contrast agents flowing quickly in the fluid is rejected for imaging. The imaging is a function of the information from contrast agents bound to tissue. The higher velocity information is mapped to black, a lower value in a dynamic range, or background B-mode information. For example, the information from bound contrast agents is colored and the information from rapidly moving contrast agents is displayed as grey scale or B-mode information is substituted.

As another example, a display or mapping methodology as described in U.S. Pat. No. 6,679,843, the disclosure of which is incorporated herein, highlights the distinguished contrast agents. Individual display indicia for each location representative of an imaged region are generated as a modulated, non-linear function of information from the slowly moving or stationary contrast agents and rapidly moving contrast agents. The non-linear function substantially maintains portions of the information associated with stationary or slowing moving tissue or contrast agents.

Figure 2:
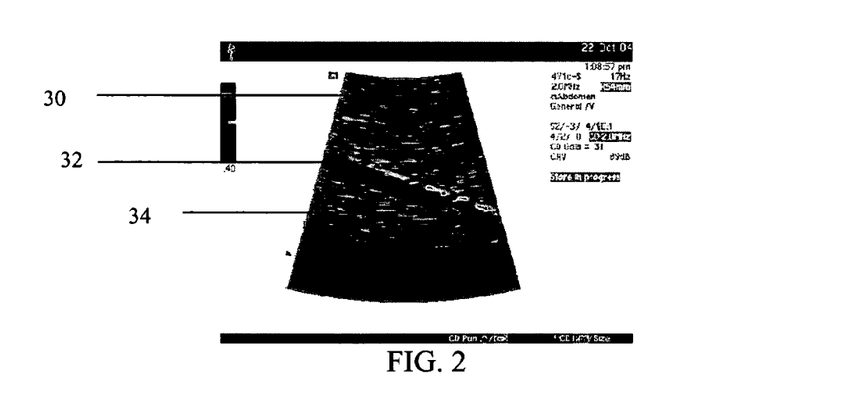
FIG. 2 is an example image generated with highlighted contrast agents.

As yet another example of highlighting, a different color scale or color is used for the different contrast agents. FIG. 2 shows a grey scale representation of an image with color information added for a vessel mimicking tube containing contrast agents within a tissue mimicking phantom. The background tissue 30 is displayed as grey scale information. Contrast agents 32, 34 are displayed in color. To de-emphasize flowing contrast agents 34 or otherwise highlight the bound contrast agents 32, different colors are provided, such as red for flowing contrast agents and gold for bound contrast agents. In FIG. 2, the bound contrast agents 32 are stuck to the top of a vessel. Velocities and/or intensities from contrast agents are mapped for imaging.

As yet another example of highlighting, a different color is used for differentiating between attached agents versus phagocytosed agents. Differentiating signal characteristics are used to assign different colors to the "stuck' bubbles versus the "engulfed" bubbles.

Since contrast agents are intravascular and can bind to tissue, tissue structure itself alternatively or additionally identifies bound contrast agent. Contrast agents adjacent to or at a same location as tissue are bound. B-mode or other mode edge detection identifies tissue structure adjacent to areas of flow, such as the heart or vessel walls. The highlighting on the image is performed as a function of the stationary or slowly moving contrast agents and tissue structure. If the stationary or slowly moving contrast agent is spaced away from tissue structure, the information at that location is not highlighted. Intensities or velocities from slowly moving or stationary contrast agents adjacent tissue structure are highlighted.

In addition or as an alternative to highlighting on an image, imaging or data processing is altered as a function of the distinguished contrast agents. For example, persistence for locations corresponding to slowly moving or stationary contrast agents is increased. Spatially adaptive persistence based on energy, velocity or intensity from contrast agents may better highlight or indicate the locations of the bound contrast agents.

With the location of bound contrast agents distinguished from other locations, contrast agent destruction ultrasound pulses are transmitted to the locations associated with the slowly moving or stationary contrast agents. The contrast agent destruction ultrasound pulses have high power, different frequency, different bandwidth, increased pulse length and/or decreased pulse repetition interval to more likely burst or destroy contrast agents. Where the contrast agents include medicine, the medicine is released by the destruction. Alternatively, the contrast agents bind to tissue to be treated with therapeutic ultrasound. The therapeutic ultrasound destroys the contrast agents as well as treats the tissue identified by the contrast agents.

The acoustic energy transmitted for destruction is minimized at locations associated with the rapidly moving contrast agents. For example, the focal point of the transmissions is placed on or by the bound contrast agents. A user places a cursor or region-of-interest (ROI) on the color-coded areas and then manually activates higher power pulses. The system uses the cursor or ROI to configure the appropriate beamforming so the higher power pulses are delivered to the color-coded regions, minimizing systemic delivery of contents. As another example, a user activates a button requesting all regions identified with a specific color to be actively interrogated with higher power pulses. The system automatically focuses lines of higher power in these regions, such as disclosed in U.S. Pat. No. 6,475,148, the disclosure of which is incorporated herein by reference. As another example, an automatic destruction pulse is delivered when the ratio of energy of the slow or stopped contrast agents to moving contrast agents is sufficiently high. The average signal energy of the identified pixels around the vessel walls versus the vessel lumen may define the ratio. Free flowing contrast agents are allowed to wash past the vessel so that only targeted agents are destroyed for drug delivery. Manual or automatically generated regions can be used.

Figure 3:
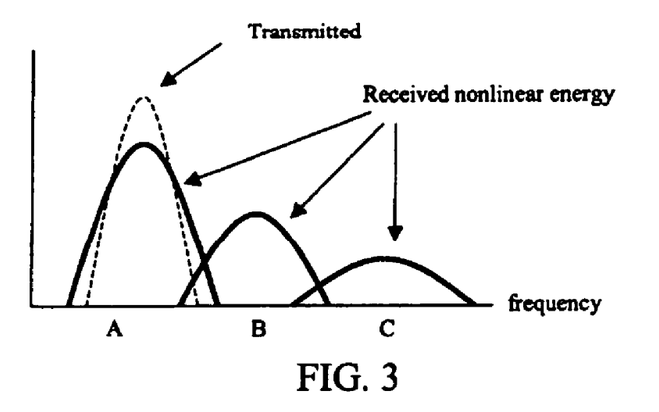
FIG. 3 is a graphical representation of received nonlinear energy responsive to contrast agents.

In another approach for characterizing contrast agents with ultrasound, a relative strength of two or more nonlinear frequency components of ultrasound signals responsive to contrast agents is determined in act 20. Nonlinear components of received signal are obtained in act 14. FIG. 3 shows a transmitted spectrum relative to received nonlinear fundamental, second harmonic and third harmonic spectra. Other relative amplitudes and spectra may be provided, such as subharmonic or ultraharmonic spectra. The relative amplitudes may also vary as a function of one or more characteristics of the contrast agents. Monitoring the relative strength of two or more nonlinear frequency components may more specifically identify different characteristics within a population of contrast agents. In alternative embodiments, the relative strength is between a linear fundamental response and a nonlinear response.

In one embodiment, multiple components or frequency bands are detected simultaneously from the same received signals after a series of transmitted pulses are detected and processed. One [transmit]×[receive] sequence is [0.5−1 0.5]×[1 1 1] where nonlinear fundamental, second harmonic, and third harmonic energy is simultaneously detected. The different components are separated or isolated by filtering. More narrowband filtering may help derive the ratios while less narrowband filtering may be used for the displayed image, helping maintain optimal spatial resolution in the displayed image.

In another embodiment, separate techniques with unique frequency bands per technique are used. Separate sequences provide the desired frequency components. To derive just component A (nonlinear fundamental, see FIG. 3), the sequence [0.5–1 1–0.5]×[–2–1 1 2] may be used since the sequence suppresses component B. Other components could be generated from a different sequence. Alternative sequences like the one above might be of interest if broad transmit pulses were desired for the best spatial resolution but only a single frequency band was desired for characterizing contrast agents. The example sequence above avoids leakage of frequencies in band B due to suppression of the frequencies in band B. To avoid leakage, the alternative sequence could be used however at the expense of lost frame rates compared to sequences with fewer transmitted pulses.

Another alternative method is to apply different weights to the received pulses to derive two or more components using the same sequence of transmitted pulses. For example, using the alternative sequence to derive just component A given above, component A is extracted. Using four receive weights of [0 1 1 0] extracts the component B without lost frame rate as additional pulses need not be transmitted.

A ratio, difference, sum, multiple, combinations thereof or other function indicates the relative strength. In one embodiment, the ratio is of second harmonic to nonlinear fundamental components of the received signals. For example, this ratio may detect attached contrast agents since attached contrast agents may exhibit a lower second harmonic-to-nonlinear-fundamental ratio. A threshold ratio distinguishes flowing contrast agents from bound contrast agents.

Figure 4:
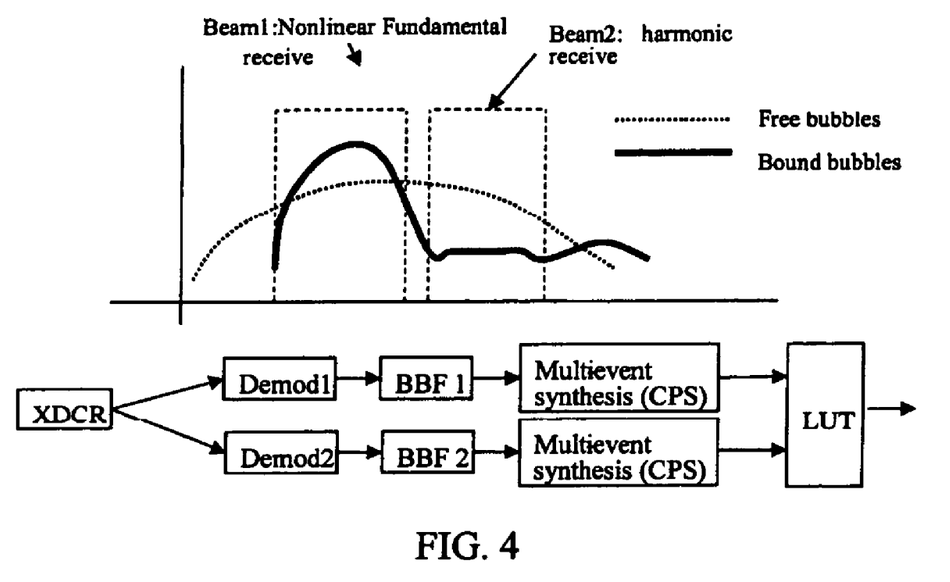
FIG. 4 is a graphical representation of differences in frequency response and associated block diagram of a system for characterizing contrast agents as a function of the differences.

FIG. 4 shows a received signal spectra and a system block diagram. In the spectral plot, two different spectra are shown, one for free flowing contrast agents and another for bound contrast agents. Contrast agents attached to endothelium or phagocytosed exhibit decreased second harmonic signal and relatively increased nonlinear fundamental signal relative to free flowing contrast agents. The dashed rectangular regions indicate the frequencies over which a filter would select one band versus another. Signals from the transducer are processed in two different paths as shown in the lower part of FIG. 4, each with a demodulation stage "demod", a baseband filter "BBF") and a contrast specific detection method (e.g., a contrast pulse sequencing "CPS" method using a multi-event synthesis operation) for isolating information at a desired frequency band. The nonlinear fundamental detection discussed above for act 14 is performed for the signals at each of the different frequency bands. A look-up table, processor or other circuit outputs the ratio. Ratio based detection alone or in combination with motion detection is used to highlight contrast agents that are stationary and exhibit decreased harmonic-to-fundamental ratio.

In another embodiment, the ratio of second harmonic to third harmonic components is determined. This ratio distinguishes between contrast agent sizes. For example, a larger ratio indicates smaller contrast agents for a given frequency and mechanical index.

In another embodiment, the ratio of two or more of the nonlinear frequency components to one or more nonlinear frequency components is determined. For example, the sum of the second and third harmonic signals in a ratio to the nonlinear fundamental signal is determined. Multiple nonlinear orders are compared to a single nonlinear order to increase information content with broader bandwidth signals containing more information. Attached contrast agents may exhibit less higher order nonlinear behavior due to damping from attached cells. Other ratio combinations are possible.

In another embodiment, the ratios distinguish between different types of contrast agents. With a abdominal transducer and a transmit frequency of 1.7 MHz for a sequence of three pulses for nonlinear imaging, sufficient energy may be available from the nonlinear fundamental A, second harmonic B, and third harmonic C components to distinguish between contrast agents by ratios. The transmit pulses have one, one and a half, two, three or other number of cycles. A longer pulse (e.g., about 3 or 4 cycles) that is more narrowband may better isolate the unique frequency components. Narrowband filtering per pulse may also isolate components. Different contrast agents may have different responses. For example, Definity, Sonovue, and Sonazoid may have different responses. Above approximately the –20 dB transmit power level relative to a maximum 0 dB level, the ratios between the different contrast agents may be similar. These transmit levels are associated with destruction of contrast agent and suggest loss-of-correlation between the transmitted pulses is the main signal component. Unique differences in nonlinearity between the microbubbles may not be detected with high confidence. Below approximately the –20 dB transmit power level, differences may allow identification of the different microbubbles using ratios. Differences in nonlinearity response may be used to characterize microbubble types. Other transducers, frequencies, filters, differences in characteristics relative to transmit power and/or transmit pulse sequences may be used.

In another embodiment, contrast agent characteristics are distinguished as a function of bandwidth. The bandwidth of the nonlinear fundamental compared to the transmitted frequency of the linear fundamental may distinguish contrast agent characteristics. For example, attached contrast agents may show less nonlinear behavior, so a measurement of the bandwidth at a specified decibel level above the noise floor indicates attachment if below a determined threshold. Further attached contrast agents may exhibit less nonlinear behavior than phagocytosed contrast agents so the bandwidth may be different. As an alternative to bandwidth, the relative center frequencies may distinguish between contrast agent characteristics. The center frequency of the linear or nonlinear fundamental signal compared to the transmitted waveform may distinguish contrast agent characteristics. For example, center frequency relationship may distinguish contrast agents captured by white blood cells or extravasated into the tissue from other contrast agents.

In act 18 of FIG. 1, an image is generated as a function of the relative strength. Spatial locations or information corresponding to the distinguished contrast agents, such as the type of agent or bound contrast agents are highlighted. For example, the signal strength of one of the components, the output of the function for determining relative strength (e.g., the ratio), or other detected values associated with the locations are mapped to the image. The mapped information is superimposed on a display, such as a B-mode or Doppler mode image, or is displayed as an independent image. Different ratios values may be highlighted on the display differently, such as using different colors. For example, a B-mode or Doppler image generated from nonlinear information is further color coded with additional unique colors highlighting the new properties or contrast agent characteristics. Alternatively, B-mode, Doppler or contrast agent information is mapped differently for locations identified for the distinguished contrast agent characteristic.

Act 22 in FIG. 1 provides another approach for characterizing contrast agents with ultrasound. Signal strength of contrast agents in a region is monitored as a function of time with ultrasound to better characterize agent behavior beyond traditional wash-in or wash-out time courses. If the signal strength of the contrast agents becomes weaker or is weaker than other contrast agents of a same type, the contrast agents may be bound. Absolute strength of returned imaging signals with or without spatial tracking indicates whether the contrast agents are bound. By comparing signals strengths of contrast agents in a same location over time, the signal strength may change due to binding. A change in signal strength from contrast agents or a threshold amount of change indicates binding. Contrast agents attached to vessel walls may expand and contract less, generating less nonlinear signals, reducing the returned nonlinear signal energy.

Contrast agents are scanned at the different times, but the return signal strength changes from the contrast agents due to a change in state. Since tissue may move, one or more locations, such as one or more regions of multiple locations, may be tracked. Speckle or structure is tracked using correlation or other similarity functions. As the contrast agent or associated tissue changes location, the contrast agent or tissue is tracked to the different locations as a function of time. The comparison of signal strength is performed for the tracked region, improving spatial registration.

In act 18, an image is generated as a function of signal strength at different times. The contrast agents with the weaker signal strength are highlighted relative to the contrast agents with the greater signal strength. Alternatively, contrast agents with greater signal strength are highlighted. Highlighting where signals from both types or states of contrast agents are color-coded includes using a different color-coding scheme rather than different brightness or other general change along a substantially linear scale. Substantially nonlinear mapping (e.g., no color for one, different colors, exponential, or other nonlinear combination) highlights contrast agents with different characteristics.

Figure 5:
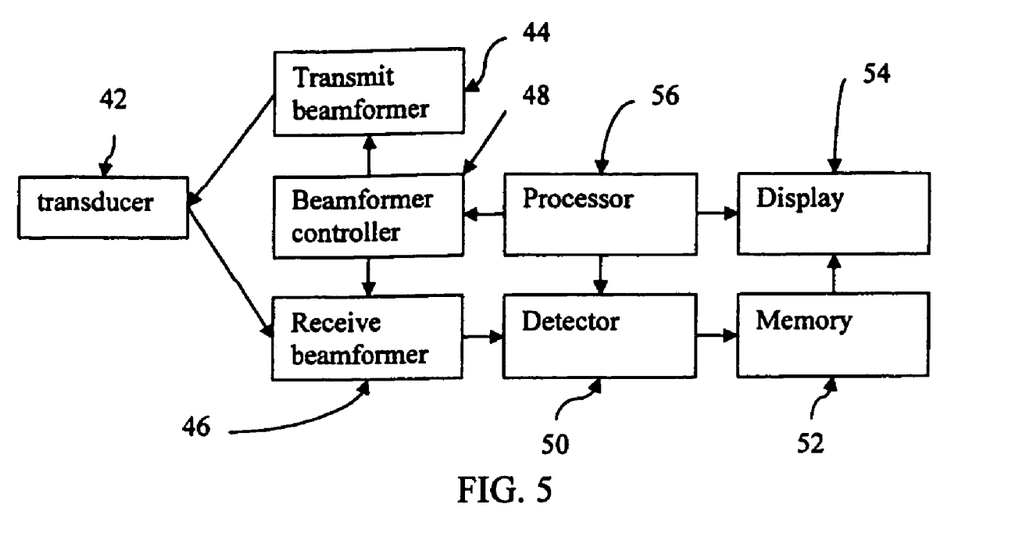
FIG. 5 is a block diagram of one embodiment of a system for characterizing contrast agents with ultrasound.

FIG. 5 shows a system for contrast agent imaging with ultrasound. The system includes transmit and receive beamformers 44, 46, a beamformer controller 48, a transducer 42, a detector 50, a memory 52, a display 54 and a processor 56. Additional, different or fewer components may be provided, such as the system without the memory 52 or with a scan converter or additional detectors. The system is a medical diagnostic ultrasound imaging system in one embodiment, but other imaging systems of the same or different modality (ultrasound) may be used. The system implements contrast pulse sequences (CPS) for obtaining information at the cubic fundamental or other detection technique for characterizing contrast agents with ultrasound.

The transmit and receive beamformers 44, 46 are ultrasound transmitter, transmit beamformer, receive beamformer, summer, filter, analog circuit, digital circuit or combinations thereof. The transmit and receive beamformers 44, 46 are operable to obtain ultrasound data representing a cubic fundamental response, such as by transmitting a sequence of pulses and receiving responsive echoes. The transmit and receive beamformers 44, 46 generate ultrasound data for each receive beam. The receiver applies appropriate phase and/or time delays to individual receive signals to cause the receive signals to add coherently from desired locations within the region of interest. By combining receive beams responsive to different ones of the pulses, cubic fundamental information is obtained. Alternatively, other nonlinear or linear responses are used.

The transducer 42 can take any desired form. The transducer 42 can be a 1-, 1.25-, 1.5-, 1.75- or 2-dimensional array of piezoelectric or capacitive membrane elements.

As described above, the amplitude and phase of transmitted signals are controlled to provide the desired contrast pulse sequence or other transmit and receive pattern or scan. The beamformer controller 48, such as a transmitter power and phase control, applies control signals to the transmit and receive beamformers 44, 46 to create transmit pulses of the desired power and phase and corresponding receive beams. Transmitter power can be varied in any suitable manner, as for example by adjusting the voltage applied to individual transducer elements, or by adjusting the number of transducer elements (or transmit aperture) used to form a particular pulse.

For obtaining ultrasound data at the nonlinear fundamental or harmonic, the receive beamformer 46 includes line memories and a summer or a filter to combine signals responsive to the transmission. Beamformed signals from the receiver are stored in the line memories or filter buffers. The line memories or buffers can be formed as physically separate memories, or alternately they can be formed as selected locations in a common physical device. The beamformed signals for a given sequence are stored in the line memories or buffers and then weighted and summed in a weighted summer. The weighted summer is controlled by the beamformer controller 48, such as a receive amplitude and phase weighting control, that provides the weighting values for both amplitude and phase that are used in the weighted summer. The memories and the summer can be implemented using analog or digital techniques. The weighted summer forms a composite output signal by weighting the separate beamformed receive signals in any of the ways described below. The composite output signal for a given spatial location is a sample associated with the nonlinear fundamental or other frequency response.

In the foregoing example, the composite output signal was formed from a weighted summation of receive signals that had been beamformed. The weighted summation can be performed at base band, intermediate frequency (IF) or radiofrequency (RF) and prior to or after beamforming. Similarly, the weighted summation can be performed either before or after scan conversion. Alternatively, a linear fundamental response is obtained with or without line memories or buffers and the summer.

The detector 50 is a B-mode detector, Doppler detector, pulsed wave Doppler detector, correlation processor, Fourier transform processor, application specific integrated circuit, general processor, control processor, field programmable gate array, digital signal processor, analog circuit, digital circuit, combinations thereof or other now known or later developed device for detecting information for display from beamformed ultrasound samples. In one embodiment, the detector 50 implements a fast Fourier transform from a plurality of samples representing a same region or gate location. Each of the samples is responsive to cubic fundamental or other nonlinear frequency so that a pulsed wave Doppler display may be generated from nonlinear response information.

In another embodiment, the detector 50 is operable to estimate velocity, direction, and/or energy values as a function of the ultrasound data or samples. Two or more samples or combined signals are input to the detector 50. The detector 50 determines the first and second coefficients of an autocorrelation function. The first order coefficient estimates energy, and the second order coefficient estimates velocity. Direction is derived from the velocity values by retaining the sign and removing the magnitude. Other calculations to estimate velocity and/or energy may be used, such as a cross-correlation or Fourier transform.

The memory 52 is a look-up table, buffer, random access memory, read only memory, combinations thereof or other now known or later developed device for storing data or a look-up table. The memory 52 is operable to store a display map. The display map may take many forms, such as separate display maps for energy, velocity, intensity, ratios, or combinations thereof. In an alternative embodiment, a processor calculates the display values from one or more input sources of data. The output data includes locations highlighted based on distinguished contrast agent characteristics.

The display 54 is a CRT, monitor, LCD, flat panel, projector or other display device. The display 54 receives display values for displaying an image. The display values are formatted as a one-dimensional image, two-dimensional image or a three dimensional representation.

The processor 56 controls the operation of the beamformer controller 48, the detector 50 and/or the memory 52. The processor 56 may generate graphics, such as text, for superposition on the image. In one embodiment, the processor 56 receives information from the detector 50 or the receive beamformer 46 for distinguishing between different characteristics. For example, the processor 56 combines contrast agent and velocity information to identify substantially stationary contrast agents. In other examples, the processor 56 determines the ratio of nonlinear frequency bands or the absolute signal strength from contrast agents. Alternatively, the receive beamformer 46, the detector 50 and/or the memory 52 implement these approaches.

The instructions for implementing the processes, methods and/or techniques discussed above are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on the computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. In a non-transitory computer readable storage medium having stored therein data representing instructions executable by a programmed processor for characterizing contrast agents with ultrasound, the storage medium comprising instructions for:
    obtaining data comprising information associated with flowing contrast agents and information associated with bound contrast agents both in a same region at a same time;
    rejecting the information associated with the flowing contrast agents in a presence of both the flowing contrast agents and bound contrast agents from the data;
    identifying, using the data resulting from the rejecting, the information associated with the bound contrast agents and not the rejected information associated with the flowing contrast agents; and
    generating an image as a function of the information associated with bound contrast agents without the information associated with the flowing contrast agents, the image representing the region and locations of the rejected information associated with the flowing contrast agents and not representing the rejected information.

2. The instructions of claim 1 wherein rejecting and identifying comprises locating the flowing and bound contrast agents as a function of nonlinear fundamental response, estimating velocities of the located flowing and bound contrast agents, and at least reducing information associated with flow velocities.

3. A method for characterizing contrast agents with ultrasound, the method comprising:
    determining, automatically, a relative strength of two or more nonlinear frequency components of ultrasound signals responsive to contrast agents in a region of a patient; and
    generating an image as a function of the relative strength.

4. The method of claim 3 wherein determining the relative strength comprises determining a ratio of second harmonic to nonlinear fundamental components.

5. The method of claim 3 wherein determining the relative strength comprises determining a ratio of second harmonic to third harmonic components.

6. The method of claim 3 wherein determining the relative strength comprises determining a ratio of two or more of the nonlinear frequency components to one or more nonlinear frequency components.

7. The method of claim 3 wherein determining comprises comparing a nonlinear bandwidth to a transmitted bandwidth.

8. The method of claim 3 wherein determining comprises measuring a received signal center frequency.

9. The method of claim 3 wherein generating comprises differentiating between attached and phagocytosed contrast agents.

10. The method of claim 3 further comprising increasing persistence as a function of the relative strength.

11. The method of claim 3 wherein generating the image comprises highlighting as a function of the signal strength.

12. The method of claim 11 wherein highlighting comprises highlighting information as a function of the signal strength and tissue structure.

13. The method of claim 3 further comprising:
    transmitting contrast agent destruction ultrasound pulses to locations associated with slowly moving or stationary contrast agents while minimizing the transmission of the contrast agent destruction ultrasound pulses to locations associated with rapidly moving contrast agents.

14. A method for characterizing contrast agents with ultrasound, the method comprising:
    monitoring signal strength of contrast agents in a two-dimensional region as a function of time with ultrasound from the two-dimensional region of a patient;
    generating an image, representing the two-dimensional region with spatial axes, where image values for spatial locations are each a function of a signal strength at different times; and
    highlighting bound versus flowing contrast agent in the image.

15. The method of claim 14 wherein monitoring comprises monitoring as a function of nonlinear components of ultrasound signals.

16. The method of claim 14 further comprising:
    spatially tracking a region as a function of time;
    wherein the monitoring is performed for the region.

17. The method of claim 14 wherein monitoring comprises identifying contrast agents with a weaker signal strength from contrast agents with a greater signal strength, and wherein generating the image comprises highlighting the contrast agents with the weaker signal strength relative to the contrast agents with the greater signal strength.

* * * * *